United States Patent
Collier et al.

(10) Patent No.: US 11,059,767 B2
(45) Date of Patent: Jul. 13, 2021

(54) PROCESS FOR THE PRODUCTION OF 2,3,3,3-TETRAFLUOROPROPENE

(71) Applicant: Arkema France, Colombes (FR)

(72) Inventors: Bertrand Collier, Montbard (FR);
Dominique Deur-Bert, Charly (FR);
Anne Pigamo, Francheville (FR);
Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 1 day.

(21) Appl. No.: 16/625,816

(22) PCT Filed: Jul. 16, 2018

(86) PCT No.: PCT/FR2018/051795
§ 371 (c)(1),
(2) Date: Dec. 23, 2019

(87) PCT Pub. No.: WO2019/016456
PCT Pub. Date: Jan. 24, 2019

(65) Prior Publication Data
US 2021/0155567 A1    May 27, 2021

(30) Foreign Application Priority Data
Jul. 17, 2017   (FR) ...................................... 1756726

(51) Int. Cl.
| C07C 17/20 | (2006.01) |
| C07C 17/25 | (2006.01) |
| B01J 23/26 | (2006.01) |
| B01J 27/132 | (2006.01) |
| C07C 21/18 | (2006.01) |

(52) U.S. Cl.
CPC ............. *C07C 17/206* (2013.01); *B01J 23/26* (2013.01); *B01J 27/132* (2013.01); *C07C 17/25* (2013.01); *C07C 21/18* (2013.01)

(58) Field of Classification Search
CPC ....... C07C 21/18; C07C 17/25; C07C 17/206; B01J 23/26; B01J 27/132
See application file for complete search history.

(56) References Cited

U.S. PATENT DOCUMENTS

| 2014/0235904 A1* | 8/2014 | Bektesevic ........... C07C 17/087 |
|  |  | 570/160 |
| 2015/0148571 A1 | 5/2015 | Chaki et al. |
| 2017/0210686 A1 | 7/2017 | Pigamo et al. |

FOREIGN PATENT DOCUMENTS

| EP | 2223906 A1 | 9/2010 |
| WO | 98/10862 A1 | 3/1998 |
| WO | 2005/037431 A1 | 4/2005 |
| WO | 2007/019353 A1 | 2/2007 |
| WO | 2016001515 A1 | 1/2016 |

OTHER PUBLICATIONS

ISA/EP; International Search Report and Written Opinion for International Patent Application No. PCT/FR2018/051795 dated Nov. 16, 2018, 10 pages.

* cited by examiner

*Primary Examiner* — Jafar F Parsa
(74) *Attorney, Agent, or Firm* — NK Patent Law

(57) ABSTRACT

The present invention relates to a process for the gas-phase production of 2,3,3,3-tetrafluoropropene, comprising the steps: i) providing a composition A comprising 2-chloro-3,3,3-trifluoropropene and/or 2,3-dichloro-1,1,1-trifluoropropane and/or 2-chloro-1,1,1,2-tetrafluoropropane or a composition B comprising 1,1,1,2,2-pentafluoropropane and/or 1,1,1,2,3-pentafluoropropane; ii) placing said composition A in contact with hydrofluoric acid in the presence of a catalytic composition comprising a chromium-based catalyst or placing said composition B in contact with a catalytic composition comprising a chromium-based catalyst to produce a composition C comprising 2,3,3,3-tetrafluoropropene, characterized in that step ii) is performed at a temperature of between 310° C. and 450° C. and in that the temperature of step ii) is controlled so as not to exceed 450° C.; and when said catalyst is deactivated, the temperature of step ii) is increased in increments from 0.5° C. to 20° C. on condition that the temperature does not exceed 450° C.

11 Claims, No Drawings

PROCESS FOR THE PRODUCTION OF 2,3,3,3-TETRAFLUOROPROPENE

CROSS-REFERENCE TO RELATED APPLICATIONS

This application is a U.S. National Stage application of International Patent Application No. PCT/FR2018/051795, filed on Jul. 16, 2018, which claims the benefit of French Patent Application No. 1756726, filed on Jul. 17, 2017.

TECHNICAL FIELD

The present invention relates to a process for producing organofluorine compounds, preferably a process for producing fluoroolefins. In particular, the present invention relates to a process for producing 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds which have a structure of use as functional materials, solvents, refrigerants, inflating agents and monomers for functional polymers or starting materials for such monomers. Hydrofluoroolefins, such as 2,3,3,3-tetrafluoropropene (HFO-1234yf), are attracting attention since they offer promising behavior as refrigerants with a low global warming potential.

Processes for producing fluoroolefins are usually performed in the presence of a starting substance, such as a chlorine-containing alkane or a chlorine-containing alkene, and in the presence of a fluorinating agent, such as hydrogen fluoride. These processes may be performed in the gas phase or in the liquid phase, in the presence or absence of a catalyst.

The gas-phase processes are usually performed in the presence of catalysts, in particular in the presence of chromium-based catalysts. US 2015/0148571 discloses a process for producing fluoroolefin in which the catalyst is highly crystalline chromium oxide. WO 2005/037431 discloses a chromium-based catalytic composition comprising $ZnCr_2O_4$ and a crystalline α-chromium oxide and its use in a process for modifying the distribution of fluorine in a halogenated hydrocarbon or for incorporating fluorine into a saturated or unsaturated hydrocarbon. WO 2007/019353 discloses the manufacture of 1,1,1,3,3-pentafluoropropane and 1,1,1,2,3-pentafluoropropane from a halopropene of formula $CX_3CCl=CClX$ in the presence of a crystalline α-chromium oxide, in which at least 0.05% of the chromium atoms in the lattice of the α-chromium oxide are replaced with a divalent copper. WO 98/10862 discloses a fluorination catalyst based on chromium(III) oxide, in which the chromium (III) oxide is at least partially and may contain a zinc atom or a compound thereof. The catalyst was used in a process for manufacturing HFC-134a. A fluorochromium oxide with a fluorine content of at least 30% by weight is also used as catalyst in a process for producing fluoroolefins as disclosed in EP 2 223 906.

There is also a need for catalytic compositions having a high activity (conversion) and/or selectivity and also for industrial chemical processes over the lifetime of a catalyst.

SUMMARY OF THE INVENTION

The present invention relates to a process for the gas-phase production of 2,3,3,3-tetrafluoropropene, comprising the steps:

i) providing a composition A comprising 2-chloro-3,3,3-trifluoropropene and/or 2,3-dichloro-1,1,1-trifluoropropane and/or 2-chloro-1,1,1,2-tetrafluoropropane or a composition B comprising 1,1,1,2,2-pentafluoropropane and/or 1,1,1,2,3-pentafluoropropane;

ii) placing said composition A in contact with hydrofluoric acid in the presence of a catalytic composition comprising a chromium-based catalyst or placing said composition B in contact with a catalytic composition comprising a chromium-based catalyst to produce a composition C comprising 2,3,3,3-tetrafluoropropene, characterized in that step ii) is performed at a temperature of between 310° C. and 450° C. and in that the temperature of step ii) is controlled so as not to exceed 450° C.; and when said catalyst is deactivated, the temperature of step ii) is increased in increments from 0.5° C. to 20° C. on condition that the temperature does not exceed 450° C.

The present invention makes it possible to prolong the service life of the catalyst and to improve the reaction efficiency by avoiding the presence of impurities generating the formation of coke.

According to a preferred embodiment, the reaction temperature used in step ii) is between 310° C. and 420° C., advantageously between 310° C. and 400° C., preferably between 310° C. and 375° C., more preferentially between 310° C. and 360° C., in particular between 330° C. and 360° C.

According to a preferred embodiment, the reaction temperature used in step ii) does not exceed 420° C., advantageously does not exceed 400° C., preferably does not exceed 375° C., more preferentially does not exceed 360° C.

According to a preferred embodiment, the temperature of step ii) is increased in increments from 0.5° C. to 15° C., advantageously from 0.5° C. to 10° C., preferably from 1° C. to 10° C., more preferentially from 1° C. to 8° C., in particular from 3° C. to 8° C.

According to a preferred embodiment, the chromium-based catalyst is a chromium oxyfluoride or a chromium oxide or a chromium fluoride.

According to a preferred embodiment, the chromium-based catalyst also comprises a cocatalyst selected from the group consisting of Ni, Zn, Co, Mn and Mg; preferably, the content of cocatalyst is between 0.01% and 10% on the basis of the total weight of the catalyst.

According to a preferred embodiment, step ii) is performed at a pressure of greater than 1.5 bara.

DETAILED DESCRIPTION OF THE INVENTION

The Applicant has observed, surprisingly, that high temperatures during the fluorination or the dehydrofluorination of the starting materials used for the production of 2,3,3,3-tetrafluoropropene may result in instability and deactivation of the catalyst used in the process, a decrease in the reaction selectivity toward the compound of interest, i.e. 2,3,3,3-tetrafluoropropene, and/or an increase in undesirable products or in impurities. Thus, the present invention provides a process for controlling the reaction temperature so as to prolong the service life of the catalyst and thus to improve the reaction efficiency.

The present invention relates to a process for the gas-phase production of 2,3,3,3-tetrafluoropropene. The process comprises a step i) of providing a composition A comprising 2-chloro-3,3,3-trifluoropropene and/or 2,3-dichloro-1,1,1-trifluoropropane and/or 2-chloro-1,1,1,2-tetrafluoropropane or a composition B comprising 1,1,1,2,2-pentafluoropropane and/or 1,1,1,2,3-pentafluoropropane.

Preferably, composition A comprises at least 20% by weight of 2-chloro-3,3,3-trifluoropropene and/or 2,3-dichloro-1,1,1-trifluoropropane and/or 2-chloro-1,1,1,2-tetrafluoropropane on the basis of the total weight of composition A, more preferentially at least 30% by weight, in particular at least 40% by weight, more particularly at least 50% by weight, preferably at least 60% by weight of 2-chloro-3,3,3-trifluoropropene and/or 2,3-dichloro-1,1,1-trifluoropropane and/or 2-chloro-1,1,1,2-tetrafluoropropane on the basis of the total weight of composition A.

Preferably, composition B comprises at least 20% by weight of 1,1,1,2,2-pentafluoropropane and/or 1,1,1,2,3-pentafluoropropane on the basis of the total weight of composition B, more preferentially at least 30% by weight, in particular at least 40% by weight, more particularly at least 50% by weight, preferably at least 60% by weight of 1,1,1,2,2-pentafluoropropane and/or 1,1,1,2,3-pentafluoropropane on the basis of the total weight of composition B.

The present process also comprises a step:
ii) placing said composition A in contact with hydrofluoric acid in the presence of a chromium-based catalyst or placing said composition B in contact with a chromium-based catalyst to produce a composition C comprising 2,3,3,3-tetrafluoropropene.

Step ii) may be performed at a temperature of between 310° C. and 449° C.; 310° C. and 448° C.; 310° C. and 447° C.; 310° C. and 446° C.; 310° C. and 445° C.; 310° C. and 444° C.; 310° C. and 443° C.; 310° C. and 442° C.; 310° C. and 441° C.; 310° C. and 440° C.; 310° C. and 439° C.; 310° C. and 438° C.; 310° C. and 437° C.; 310° C. and 436° C.; 310° C. and 435° C.; 310° C. and 434° C.; 310° C. and 433° C.; 310° C. and 432° C.; 310° C. and 431° C.; 310° C. and 430° C.; 310° C. and 429° C.; 310° C. and 428° C.; 310° C. and 427° C.; 310° C. and 426° C.; 310° C. and 425° C.; 310° C. and 424° C.; 310° C. and 423° C.; 310° C. and 422° C.; 310° C. and 421° C.

According to a preferred embodiment, the reaction temperature used in step ii) is between 310° C. and 420° C. Advantageously, the reaction temperature used in step ii) is between 310° C. and 419° C.; 310° C. and 418° C.; 310° C. and 417° C.; 310° C. and 416° C.; 310° C. and 415° C.; 310° C. and 414° C.; 310° C. and 413° C.; 310° C. and 412° C.; 310° C. and 411° C.; 310° C. and 410° C.; 310° C. and 409° C.; 310° C. and 408° C.; 310° C. and 407° C.; 310° C. and 406° C.; 310° C. and 405° C.; 310° C. and 404° C.; 310° C. and 403° C.; 310° C. and 402° C.; 310° C. and 401° C.; 310° C. and 400° C. Preferably, the reaction temperature used in step ii) is between 310° C. and 398° C.; 310° C. and 396° C.; 310° C. and 394° C.; 310° C. and 392° C.; 310° C. and 390° C.; 310° C. and 388° C.; 310° C. and 386° C.; 310° C. and 384° C.; 310° C. and 382° C.; 310° C. and 380° C.; 310° C. and 378° C.; 310° C. and 376° C.; 310° C. and 375° C. More preferentially, the reaction temperature used in step ii) is between 310° C. and 374° C. or 310° C. and 372° C. or 310° C. and 370° C. or 310° C. and 368° C. or 310° C. and 366° C. or 310° C. and 364° C. or 310° C. and 362° C. or 310° C. and 360° C. In particular, the reaction temperature used in step ii) is between 311° C. and 360° C.; 312° C. and 360° C.; 313° C. and 360° C.; 314° C. and 360° C.; 315° C. and 360° C.; 316° C. and 360° C.; 317° C. and 360° C.; 318° C. and 360° C.; 319° C. and 360° C.; 320° C. and 360° C.; 321° C. and 360° C.; 322° C. and 360° C.; 323° C. and 360° C.; 324° C. and 360° C.; 325° C. and 360° C.; 326° C. and 360° C.; 327° C. and 360° C.; 328° C. and 360° C.; 329° C. and 360° C.; 330° C. and 360° C.

Advantageously, the reaction temperature used in step ii) does not exceed 450° C., does not exceed 449° C., does not exceed 448° C., does not exceed 447° C., does not exceed 446° C., does not exceed 445° C., does not exceed 444° C., does not exceed 443° C., does not exceed 442° C., does not exceed 441° C., does not exceed 440° C., does not exceed 439° C., does not exceed 438° C., does not exceed 437° C., does not exceed 436° C., does not exceed 435° C., does not exceed 434° C., does not exceed 433° C., does not exceed 432° C., does not exceed 431° C., does not exceed 430° C., does not exceed 429° C., does not exceed 428° C., does not exceed 427° C., does not exceed 426° C., does not exceed 425° C., does not exceed 424° C., does not exceed 423° C., does not exceed 422° C., does not exceed 421° C.

Preferably, the reaction temperature used in step ii) does not exceed 420° C., does not exceed 419° C., does not exceed 418° C., does not exceed 417° C., does not exceed 416° C., does not exceed 415° C., does not exceed 414° C., does not exceed 413° C., does not exceed 412° C., does not exceed 411° C., does not exceed 410° C., does not exceed 409° C., does not exceed 408° C., does not exceed 407° C., does not exceed 406° C., does not exceed 405° C., does not exceed 404° C., does not exceed 403° C., does not exceed 402° C., does not exceed 401° C., does not exceed 400° C., does not exceed 399° C., does not exceed 398° C., does not exceed 397° C., does not exceed 396° C., does not exceed 395° C., does not exceed 394° C., does not exceed 393° C., does not exceed 392° C., does not exceed 391° C., does not exceed 390° C., does not exceed 389° C., does not exceed 388° C., does not exceed 387° C., does not exceed 386° C., does not exceed 385° C., does not exceed 384° C., does not exceed 383° C., does not exceed 382° C., does not exceed 381° C., does not exceed 380° C., does not exceed 379° C., does not exceed 378° C., does not exceed 377° C., does not exceed 376° C., does not exceed 375° C., does not exceed 374° C., does not exceed 373° C., does not exceed 372° C., does not exceed 371° C., does not exceed 370° C., does not exceed 369° C., does not exceed 368° C., does not exceed 367° C., does not exceed 366° C., does not exceed 365° C., does not exceed 364° C., does not exceed 363° C., does not exceed 362° C., does not exceed 361° C. or does not exceed 360° C.

According to a preferred embodiment, the temperature of step ii) is increased in increments of 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6.0° C., 6.1° C., 6.2° C., 6.3° C., 6.4° C., 6.5° C., 6.6° C., 6.7° C., 6.8° C., 6.9° C., 7.0° C., 7.1° C., 7.2° C., 7.3° C., 7.4° C., 7.5° C., 7.6° C., 7.7° C., 7.8° C., 7.9° C., 8.0° C., 8.1° C., 8.2° C., 8.3° C., 8.4° C., 8.5° C., 8.6° C., 8.7° C., 8.8° C., 8.9° C., 9.0° C., 9.1° C., 9.2° C., 9.3° C., 9.4° C., 9.5° C., 9.6° C., 9.7° C., 9.8° C., 9.9° C., 10.0° C., 10.1° C., 10.2° C., 10.3° C., 10.4° C., 10.5° C., 10.6° C., 10.7° C., 10.8° C., 10.9° C., 11.0° C., 11.1° C., 11.2° C., 11.3° C., 11.4° C., 11.5° C., 11.6° C., 11.7° C., 11.8° C., 11.9° C., 12.0° C., 12.1° C., 12.2° C., 12.3° C., 12.4° C., 12.5° C., 12.6° C., 12.7° C., 12.8° C., 12.9° C., 13.0° C., 13.1° C., 13.2° C., 13.3° C., 13.4° C., 13.5° C., 13.6° C., 13.7° C., 13.8° C., 13.9° C., 14.0° C., 14.1° C., 14.2° C., 14.3° C., 14.4° C., 14.5° C., 14.6° C., 14.7° C., 14.8° C., 14.9° C., 15.0° C., 15.1° C., 15.2° C., 15.3° C., 15.4° C., 15.5° C., 15.6° C., 15.7° C., 15.8° C., 15.9° C., 16.0° C., 16.1° C., 16.2° C., 16.3° C., 16.4° C., 16.5° C., 16.6° C., 16.7° C., 16.8° C., 16.9° C., 17.0° C., 17.1° C., 17.2° C., 17.3° C., 17.4° C., 17.5° C., 17.6° C., 17.7° C., 17.8° C., 17.9° C., 18.0° C., 18.1° C., 18.2° C., 18.3° C., 18.4° C., 18.5° C., 18.6° C., 18.7° C., 18.8° C., 18.9° C., 19.0° C., 19.1° C., 19.2° C., 19.3° C., 19.4° C., 19.5° C., 19.6° C., 19.7° C., 19.8° C., 19.9° C. or 20.0° C.

According to a preferred embodiment, the temperature of step ii) is increased in increments from 0.5° C. to 20° C., from 0.5° C. to 19° C., from 0.5° C. to 18° C., from 0.5° C. to 17° C., from 0.5° C. to 16° C. or from 0.5° C. to 15° C. Advantageously, the temperature of step ii) is increased in increments from 0.5° C. to 14° C., from 0.5° C. to 13° C., from 0.5° C. to 12° C., from 0.5° C. to 11° C. or from 0.5° C. to 10° C. Preferably, the temperature of step ii) is increased in increments from 0.6° C. to 10° C., from 0.7° C. to 10° C., from 0.8° C. to 10° C., from 0.9° C. to 10° C. or from 1° C. to 10° C. More preferentially, the temperature of step ii) is increased in increments from 1° C. to 9° C. or from 1° C. to 8° C. In particular, the temperature of step ii) is increased in increments from 2° C. to 8° C. or from 3° C. to 8° C.

In this process, the catalytic composition comprises a chromium-based catalyst. Preferably, the chromium-based catalyst may be a chromium oxide (for example $CrO_2$, $CrO_3$ or $Cr_2O_3$), a chromium oxyfluoride or a chromium fluoride (for example $CrF_3$) or a mixture thereof. The chromium oxyfluoride may have a fluorine content of between 1% and 60% by weight on the basis of the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight of fluorine on the basis of the total weight of chromium oxyfluoride. The catalytic composition may also comprise a cocatalyst chosen from the group consisting of Ni, Co, Zn, Mg, Mn, Fe, Zn, Ti, V, Zr, Mo, Ge, Sn, Pb, Sb; preferably Ni, Co, Zn, Mg, Mn; in particular Ni, Co, Zn. The weight content of the cocatalyst is between 1% and 10% by weight on the basis of the total weight of the catalytic composition. The catalytic composition may also comprise a support such as alumina, for example in its alpha form, activated alumina, aluminium halides (for example $AlF_3$), aluminium oxyhalides, active charcoal, magnesium fluoride or graphite. Preferably, the catalytic composition has a specific surface area of between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to a preferred embodiment, step ii) is performed at atmospheric pressure or at a pressure above atmospheric pressure, advantageously at a pressure of greater than 1.5 bara, preferably at a pressure of greater than 2.0 bara, in particular at a pressure of greater than 2.5 bara, more particularly at a pressure of greater than 3.0 bara.

Preferably, step ii) is performed at a pressure between atmospheric pressure and 20 bara, preferably between 2 and 18 bara, more preferentially between 3 and 15 bara.

Preferably, step ii) of the present process is performed with a contact time of between 1 and 100 seconds, preferably between 2 and 75 seconds, in particular between 3 and 50 seconds. The process may be conducted over a period of between 10 and 8000 hours, preferably between 50 and 5000 hours, more preferentially between 70 and 1000 hours. An oxidant, such as oxygen or chlorine, may be added during the process. The mole ratio of the oxidant to the hydrocarbon compound may be between 0.005 and 2, preferably between 0.01 and 1.5. The oxidant may be pure oxygen, air, or a mixture of oxygen and nitrogen.

As mentioned above, composition A is placed in contact with hydrofluoric acid in the presence of a catalytic composition as described above. Preferably, the HF/composition A mole ratio may vary between 1:1 and 150:1, preferably between 2:1 and 125:1, more preferentially between 3:1 and 100:1. In this case, the number of moles of all of the organic compounds constituting composition A is taken into account for the calculation of this mole ratio. In particular, the HF/2-chloro-3,3,3-trifluoropropene and/or 2,3-dichloro-1,1,1-trifluoropropane and/or 2-chloro-1,1,1,2-tetrafluoropropane mole ratio may vary between 1:1 and 150:1, preferably between 2:1 and 125:1, more preferentially between 3:1 and 100:1.

Hydrochloric acid may be produced during the implementation of step ii) with composition A. Composition C may comprise, besides 2,3,3,3-tetrafluoropropene, HCl, unreacted HF and optionally unreacted 2-chloro-3,3,3-trifluoropropene and/or 2,3-dichloro-1,1,1-trifluoropropane and/or 2-chloro-1,1,1,2-tetrafluoropropane. Composition C may also comprise 1,1,1,2,2-pentafluoropropane.

Composition C may be purified, for example by distillation, under conditions that are effective for forming a stream C1 comprising HCl and 2,3,3,3-tetrafluoropropene and optionally 1,1,1,2,2-pentafluoropropane and a stream C2 comprising HF and 2-chloro-3,3,3-trifluoropropene and/or 2,3-dichloro-1,1,1-trifluoropropane and/or 2-chloro-1,1,1,2-tetrafluoropropane and optionally 1,1,1,2,2-pentafluoropropane. Alternatively, composition C may be purified, for example by distillation, under conditions that are effective for forming a stream Cr comprising HCl and a stream C2' comprising HF, 2,3,3,3-tetrafluoropropene and 2-chloro-3,3,3-trifluoropropene and/or 2,3-dichloro-1,1,1-trifluoropropane and/or 2-chloro-1,1,1,2-tetrafluoropropane and optionally 1,1,1,2,2-pentafluoropropane. Alternatively, composition C may be purified, for example by distillation, under conditions that are effective for forming a stream C1" comprising HCl, 2,3,3,3-tetrafluoropropene and 2-chloro-3,3,3-trifluoropropene and/or 2,3-dichloro-1,1,1-trifluoropropane and/or 2-chloro-1,1,1,2-tetrafluoropropane and optionally 1,1,1,2,2-pentafluoropropane and a stream C2" comprising H F.

Stream C1 or stream C1" may be distilled to remove the hydrochloric acid and to form a composition C3 comprising 2,3,3,3-tetrafluoropropene and optionally 1,1,1,2,2-pentafluoropropane or a composition C3" comprising 2,3,3,3-tetrafluoropropene and 2-chloro-3,3,3-trifluoropropene and/or 2,3-dichloro-1,1,1-trifluoropropane and/or 2-chloro-1,1,1,2-tetrafluoropropane and optionally 1,1,1,2,2-pentafluoropropane.

Step ii) may be performed with composition B with or without hydrofluoric acid. If hydrofluoric acid is present, the HF/composition B mole ratio may vary between 1:1 and 150:1, preferably between 2:1 and 125:1, more preferentially between 3:1 and 100:1. In this case, the number of moles of all of the organic compounds constituting composition B is taken into account for the calculation of this mole ratio. In particular, the HF/1,1,1,2,2-pentafluoropropane and/or 1,1,1,2,3-pentafluoropropane mole ratio may vary between 1:1 and 150:1, preferably between 2:1 and 125:1, more preferentially between 3:1 and 100:1.

Preferably, hydrofluoric acid is produced during the implementation of step ii) with composition B. Composition C may comprise, besides 2,3,3,3-tetrafluoropropene, HF and optionally unreacted 1,1,1,2,2-pentafluoropropane and/or 1,1,1,2,3-pentafluoropropane.

Composition C may be purified, for example by distillation, under conditions that are effective for forming a stream C4 comprising 1,1,1,2,2-pentafluoropropane and/or 1,1,1,2,3-pentafluoropropane and 2,3,3,3-tetrafluoropropene and a stream C5 comprising HF.

Alternatively, composition C may be purified, for example by distillation, under conditions that are effective for forming a stream C4' comprising 2,3,3,3-tetrafluoropropene and a stream C5' comprising HF and 1,1,1,2,2-pentafluoropropane and/or 1,1,1,2,3-pentafluoropropane.

A polymerization inhibitor may be used to improve the service life of the catalyst, typically in a concentration of from 50 to 1000 ppm, preferably from 100 to 500 ppm on the basis of the total weight of composition A or B. The polymerization inhibitor may be p-methoxyphenol, t-amylphenol, limonene, d,l-limonene, quinones, hydroquinones, epoxides, amines, phosphates or phosphorothionates, or mixtures thereof.

Example 1 (Comparative)

The fluorination of HCFO-1233xf to HFO-1234yf (2,3,3,3-tetrafluoropropene) and optionally to 1,1,1,2,2-pentafluoropropane is performed in a multitubular reactor with a certain degree of conversion. A recycling loop of controlled flow rate makes it possible to return certain products into the fluorination reactor. The reactor contains a bulk catalyst based on chromium oxide. The catalyst is activated by means of a series of steps comprising drying, fluorination, treatment under air and fluorination with recycling. This multi-step treatment makes it possible to render the catalytic solid active and selective.

The fluorination process is performed under the following operating conditions:
   An absolute pressure in the fluorination reactor of 6 bar absolute
   A mole ratio between HF and the sum of the organic materials fed in via the recycling loop of between 11 and 13
   A contact time of between 18 and 20 seconds
   A constant temperature in the reactor of 350° C.

The initial degree of conversion of the HCFO-1233xf is greater than 72%. A final degree of conversion of 41% is achieved after 616 hours of functioning.

Example 2

The process according to the invention is performed in the same manner as in example 1 with the following operating conditions:
   An absolute pressure in the fluorination reactor of 6 bar absolute
   A mole ratio between HF and the sum of the organic materials fed in via the recycling loop of between 11 and 13
   A contact time of between 18 and 20 seconds
   A starting temperature in the reactor of 330° C. followed by a gradual increase in temperature in increments of 5° C.:
   At time t=151 hours, the reactor temperature is set at 335° C.,
   At time t=323 hours, the reactor temperature is set at 340° C.,
   At time t=457 hours, the reactor temperature is set at 345° C.,
   At time t=599 hours, the reactor temperature is set at 350° C.

The initial degree of conversion of the HCFO-1233xf is greater than 72%. A final degree of conversion of 41% is achieved after 670 hours of functioning, i.e. a gain of 10%.

The invention claimed is:

1. A process for the gas-phase production of 2,3,3,3-tetrafluoropropene, comprising the steps:
   i. providing a composition A comprising 2-chloro-3,3,3-trifluoropropene and/or 2,3-dichloro-1,1,1-trifluoropropane and/or 2-chloro-1,1,1,2-tetrafluoropropane or a composition B comprising 1,1,1,2,2-pentafluoropropane and/or 1,1,1,2,3-pentafluoropropane;
   ii. placing said composition A in contact with hydrofluoric acid in the presence of a catalytic composition comprising a chromium-based catalyst or placing said composition B in contact with a catalytic composition comprising a chromium-based catalyst to produce a composition C comprising 2,3,3,3-tetrafluoropropene, wherein step ii) is performed at a temperature of between 310° C. and 450° C. and the temperature of step ii) is controlled so as not to exceed 450° C.; and when said catalyst is deactivated, the temperature of step ii) is increased in increments from 0.5° C. to 20° C. on condition that the temperature does not exceed 450° C.

2. The process as claimed in claim 1, wherein the reaction temperature used in step ii) is between 310° C. and 420° C.

3. The process as claimed in claim 1, wherein the reaction temperature used in step ii) does not exceed 420° C.

4. The process as claimed in claim 1, wherein the temperature of step ii) is increased in increments from 0.5° C. to 15° C.

5. The process as claimed in claim 1, wherein the chromium-based catalyst is a chromium oxyfluoride or a chromium oxide or a chromium fluoride.

6. The process as claimed in claim 1, wherein the chromium-based catalyst also comprises a cocatalyst selected from the group consisting of Ni, Zn, Co, Mn and Mg.

7. The process as claimed in claim 1, wherein step ii) is performed at a pressure of greater than 1.5 bara.

8. The process as claimed in claim 6, wherein a content of cocatalyst is between 0.01% and 10% on the basis of the total weight of the catalyst.

9. The process as claimed in claim 4, wherein the temperature of step ii) is increased in increments from 1° C. to 10° C.

10. The process as claimed in claim 2, wherein the reaction temperature used in step ii) is between 310° C. and 375° C.

11. The process as claimed in claim 3, wherein the reaction temperature used in step ii) does not exceed 400° C.

* * * * *